United States Patent [19]

Redmann

[11] Patent Number: 4,638,674
[45] Date of Patent: Jan. 27, 1987

[54] SAMPLE-COLLECTING DEVICE FOR GASEOUS OR VAPOROUS CONDENSABLE RADIOACTIVE SUBSTANCES, ESPECIALLY FOR COLLECTING TRACES OF TRITIUM

[75] Inventor: Eckhard Redmann, Frankfurt, Fed. Rep. of Germany

[73] Assignee: Kraftwerk Union Aktiengesellschaft, Mülheim an der Ruhr, Fed. Rep. of Germany

[21] Appl. No.: 617,634

[22] Filed: Jun. 6, 1984

[30] Foreign Application Priority Data

Jun. 10, 1983 [DE] Fed. Rep. of Germany ....... 3321063

[51] Int. Cl.$^4$ .............................................. G01N 1/24
[52] U.S. Cl. ............................. 73/863.12; 73/863.03; 73/863.23; 340/584; 340/606; 340/613; 340/679
[58] Field of Search ........... 73/863.12, 863.03, 863.02, 73/863.01, 863.11, 863.21, 863.23; 374/157

[56] References Cited

U.S. PATENT DOCUMENTS

| | | | |
|---|---|---|---|
| 1,364,035 | 12/1920 | Carter, Jr. ..................... | 73/863.03 X |
| 2,306,606 | 12/1942 | Hirsch ......................... | 73/863.12 X |
| 2,687,185 | 8/1954 | McChesney ................... | 73/863.12 |
| 3,372,274 | 3/1968 | Landolt ....................... | 73/863.23 X |
| 3,748,906 | 7/1973 | Manka ......................... | 73/863.01 |
| 3,938,390 | 2/1976 | Grey ........................... | 73/863.11 |
| 3,985,624 | 10/1976 | Prevost et al. ................ | 73/863.12 |
| 4,147,500 | 4/1979 | Karlsoen ...................... | 73/863.12 |
| 4,191,541 | 3/1980 | Jenkins ........................ | 73/863.12 |
| 4,386,534 | 6/1983 | Englund et al. ................ | 73/863.01 |
| 4,389,903 | 6/1983 | Bertone et al. ................ | 73/863.23 X |

FOREIGN PATENT DOCUMENTS

| | | | |
|---|---|---|---|
| 2905981 | 9/1980 | Fed. Rep. of Germany ... | 73/863.03 |
| 208642 | 12/1983 | Japan ........................... | 73/863.83 |

OTHER PUBLICATIONS

"Sulphur Isotope Ratios of Some Power Plant Flue Gases; A Method for Collecting the Sulphur Oxide"; *Journal of Applied Chemistry and Biotechnology;* vol. 23, No. 12, pp. 855–863; Dec. 1974; J. Forrest et al.

"A Simple Sampler to Monitor Sulphur Oxide Emissions from a Cement Works"; *Atmospheric Environment;* vol. 9, No. 1; Jan. 1975; pp. 131–133; R. A. Barnes.

"Pumping Gas Samples Containing Condensible Vapors"; *ISA Transactions;* vol. 17, No. 4; 1978; pp. 55–60; Charles G. Heisig.

*Primary Examiner*—Jerry W. Myracle
*Assistant Examiner*—Tom Noland
*Attorney, Agent, or Firm*—Herbert L. Lerner; Laurence A. Greenberg

[57] ABSTRACT

Sample collecting system for gaseous or vaporous condensable radioactive substances contained in the ambient air, especially for collecting traces of tritium via the $T_2O$ vapor content in the exhaust air of a nuclear plant. A gas stream of exhaust air is filtered and the filtered gas continues its flow through a suction branch line containing a measuring gas pump which propels the gas stream into and through a precipitate line. The precipitate line, enclosed in a measuring-gas cooler which is a cooling chamber, extends downward and then upward and then out of the cooling chamber, through a measuring-gas choke, through a flow transducer and the gas stream then returned to the exhaust gas flue or ambient air. The pump feeding the precipitate line has its pressure maintained constant by a bypass line and a pressure difference control valve from the output side of the flow transducer to the discharge side of the pump. The cooling temperature of the measurement gas cooler is monitored with an alarm signal if the temperature limit is exceeded. The condensate collecting tank of the $T_2O$ also acts as part of the mechanism in determining liquid level in the tank.

11 Claims, 2 Drawing Figures

SAMPLE-COLLECTING DEVICE FOR GASEOUS OR VAPOROUS CONDENSABLE RADIOACTIVE SUBSTANCES, ESPECIALLY FOR COLLECTING TRACES OF TRITIUM

BACKGROUND OF THE INVENTION

1. Field of the Invention

The invention relates to a sample-collecting system for gaseous or vaporous condensable radioactive substances contained in the ambient air, especially for collecting traces of tritium via the $T_2O$ vapor content contained in the exhaust air of a nuclear installation or a nuclear power generating station.

2. Description of the Prior Art

According to the safety rules of the Nuclear Engineering Committee (KTA), part 1: Measurement and Monitoring of the discharge of radioactive substance in the flue exhaust gas during the intended operation, it is stated (KTA 1503.1, version of February, 1979) with regard to tritium monitoring that tritium samples are to be taken continuously from the flue exhaust air and to be evaluated quarterly, and specifically in light-water and high-temperature reactors.

Tritium is the heaviest hydrogen isotope. Its atomic weight is 3.01686 (referred to $^{12}C$); it is radioactive. In nuclear installations and, in particular, in nuclear power plants, traces of tritium are discharged into the environment with the exhaust air. Conclusions as to the operating state of the reactor can be drawn from the amount of tritium traces. In nuclear installations and, in particular nuclear power stations, the tritium traces contained in the exhaust air must be monitored, as mentioned, reliably over extended periods of time and the collected samples must then be subjected to laboratory tests. This is generally not done at the site where the sample is taken, but in a laboratory remote therefrom. A particular problem involved in such a sample-collecting device is that as few as possible or no manual operations are to be performed during the sample-taking interval in the device. The operation of the sample-collecting device should be intrinsically safe as far as possible, requiring only that the collected sample be removed at the end of the sample taking interval and exchanged for an empty exchanged vessel. Such a continuous sample taking operation puts more stringent requirements on the pneumatic-hydraulic as well as on the electrical system of the sample collecting device.

SUMMARY OF THE INVENTION

An object of the invention is to provide a sample-collecting system of the kind defined at the outset which meets the stated requirements in an advantageous manner, i.e., operates intrinsically safely over an extended monitoring period and, in the event disturbances occur, gives at least one trouble signal to the control room. Of special importance, however, is the sample collecting system as a whole which is, in general, trouble-free with relatively little difficulties due particularly to the arrangement and features of the system. With the foregoing and other objects in view, there is provided in accordance with the invention a sample collecting system for collecting gaseous or vaporous condensable radioactive substances in air which will operate over an extended monitoring period with no or few disturbances, and in the event that a disturbance occurs, gives at least one trouble signal, which comprises (a) a fine filter through which a gas stream of air containing gaseous or vaporous condensable radioactive substances passes for removal of entrained particles suspended in the gas stream (b) at least one suction branch line into which the filtered gas stream flows (c) a measuring gas pump in the suction branch line propelling the gas stream from the suction branch line through a precipitate line enclosed in a measuring gas cooler, said precipitate line extending downwardly in the measuring gas cooler, at least partially as a helical coil for condensing the condensable radioactive substances together with $H_2O$ if present and aiding in separating the condensate from the uncondensed gas in the gas stream (d) a condensate collecting point at about the lowest point of the precipitate line for discharge of the condensate from the precipitate line (e) a rising gas branch from the condensate collecting point upwards and then out of the measuring gas cooler for conducting the uncondensed gas from the condensate collecting point (f) a measuring gas choke in the measuring gas line for determining the flow resistance in that line, followed by a transducer which aids in controlling the gas mass flow, and following the transducer, the gas therefrom is returned to the source from which the gas stream for sampling was withdrawn (g) a pressure measuring line with a presure-difference control valve from the output of the flow transducer to the input of the precipitate line for regulating the measuring gas pressure of the measuring gas pump at the input of the precipitate line (h) at least one temperature sensor in the measuring gas cooler and temperature indicating means outside the measuring gas cooler for ascertaining the temperature and indicating temperature limit values, at least indicating if an upper temperature is exceeded (i) a fine separator system into which the condensate from the collecting point at the low point of the precipitate line flows (j) a condensate line with a drain valve through which the condensate from the fine separator system discharges (k) a condensate collecting tank located underneath the fine separator system and into which the condensate from the condensate line flows, said tank also acting in determining the liquid level therein.

Other features which are considered as characteristic for the invention are set forth in the appended claims.

Although the invention is illustrated and described herein as embodied in sample-collecting device for gaseous or vaporous condensable radioactive substances, especially for collecting traces of tritium, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings in which.

DETAILED DESCRIPTION OF THE INVENTION

Figure 1:
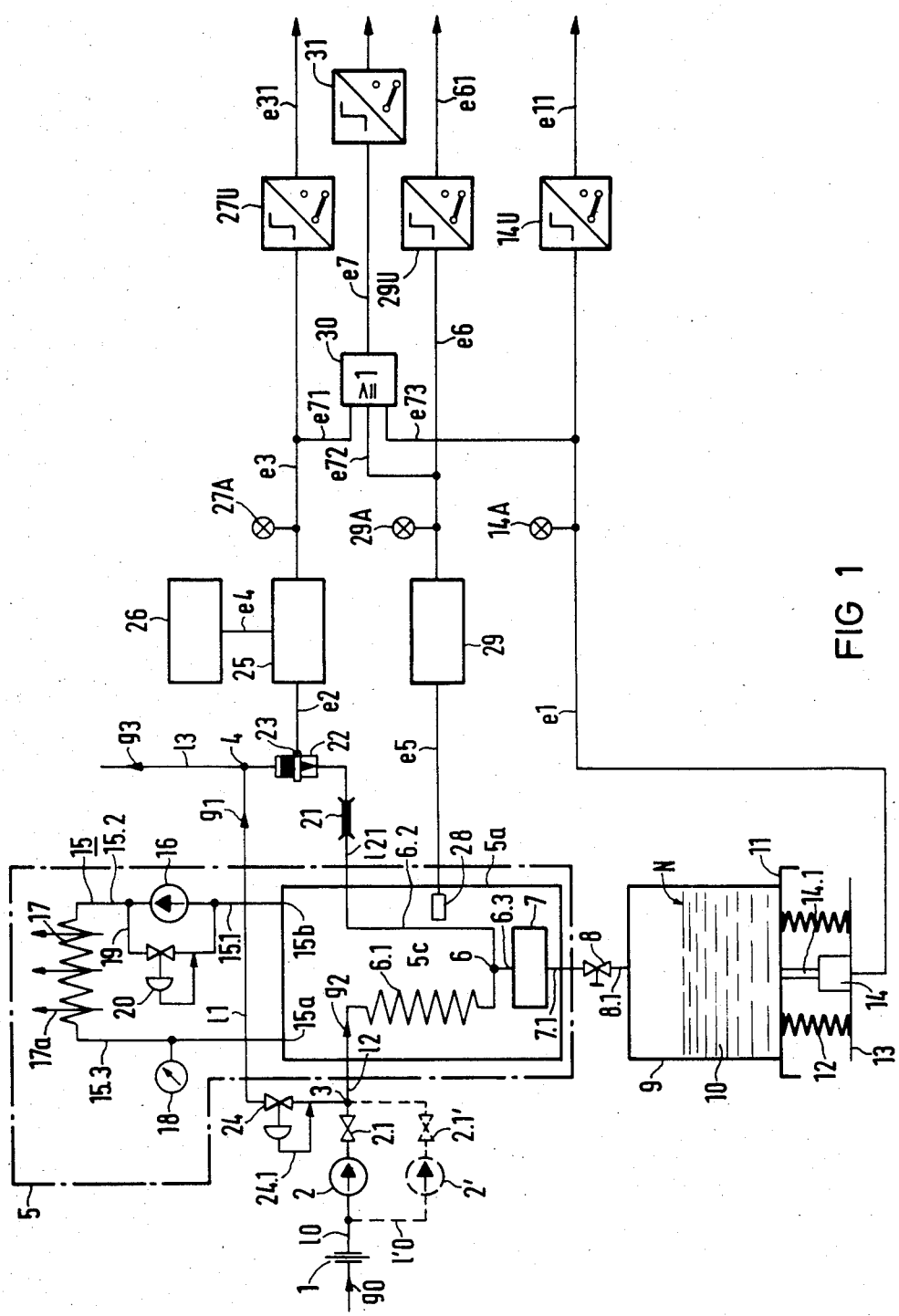
FIG. 1 shows a wiring diagram of the sample-collecting system with its pneumatic, hydraulic and electrical components as well as connecting lines.

In accordance with the invention, a gas stream of ambient air or exhaust air from a nuclear installation or a nuclear power plant containing gaseous or vaporous condensable radioactive substances is filtered in a fine filter to remove entrained particles and the filtered gas continues its flow through a suction branch line containing a measuring gas pump which propels the gas stream into and through a precipitate line. The precipitate line, enclosed in a measuring gas cooler which is a cooling chamber, extends downward and then upward and then out of the cooling chamber, through a measuring gas choke, through a flow transducer and the gas stream then returned to the exhaust gas flue or ambient air. At the lowest point of the precipitate line which is shaped at least partially as a helical tube coil, is located a fine separator system which leads via a condensate discharge line with a drain valve into a condensate collecting tank located underneath, which tank acts as a filling level indicator. For regulating the measuring gas pressure of the measuring gas pump at the input of the precipitate line carrying the initial pressure on the pump pressure output, the measuring gas pressure prevailing at the output of the flow transducer is returned to the pressure output of the measuring gas pump via a pressure measuring line and a pressure difference control valve. In the cooling chamber of the measuring gas cooler, through which the coolant flows and through which the precipitate line passes, at least one temperature sensor arrangement is installed which ascertains the actual temperature value and indicates limit values, at least if an upper temperature limit is exceeded.

The advantages attainable with the invention are achieved by the combinative effect of a number of measures: Due to the fact that the measurement gas pump pushes the measurement gas through the precipitation line or lines and these lines are followed by a choke as well as by the flow transducer, the pump has always a defined initial pressure on its output (pressure) side which is held constant by the actual pressure state after the flow transducer in the sense of a constant mass flow control by the provision that one pressure measuring line is fed-back as a bypass line from the output of the flow transducer to the output side of the pump via a pressure difference control valve or a bypass pressure regulator. The cooling temperature of the measurement gas cooler is monitored; if it is exceeded, an alarm signal is given because then, the tritium condensation would be jeopardized. If the measurement gas cooler temperature falls below (a given value), this need not absolutely be monitored by a separate temperature sensor because this disturbance is also covered by the flow monitor (the flow would drop if the lines are frozen). However, a separate temperature sensor can, of course, also be provided to monitor if the temperature drops below the permissible measuring gas cooler temperature. The mentioned flow transducer is preferably supervised with respect to whether the values are above or below the permissible flow values by a ring initiator which, in both of these cases, gives a warning signal and interrupts the operating-hours counter.

In the following, the invention will be explained in further detail with the aid of an embodiment example shown in the drawings.

According to FIG. 1, a gas stream $g_o$ taken from the flue exhaust air (the flue itself is not shown,) is transported via the suction branch L0 with a fine filter 1, followed by a measuring gas pump 2, to the branching point 3, from which on the one hand, the bypass line L1 and, on the other hand, the measuring gas line L2 lead to the line-collecting or nodal point, 4, from which the gas streams $g_1$ and $g_2$ are pushed as a total stream $g_3$ back into the exhaust gas flue through the line L3. At least one second suction branch L'0 can be provided, to which the connection is switched in the event of a disturbance in the first measuring gas pump 2. It is indicated by the second measuring gas pump 2' which is connected parallel to the measuring gas pump 2 and is shown by dashed lines as well as by the shut-off valves 2.1, 2.1' respectively connected in series with the two measuring gas pumps. In this case, the disturbed branch is turned off by its shut-off valve 2.1 until the trouble is corrected. During this time, the spare branch 1'0 is operative. The latter is then shut off when the main branch 10 is switched on again.

Figure 2:
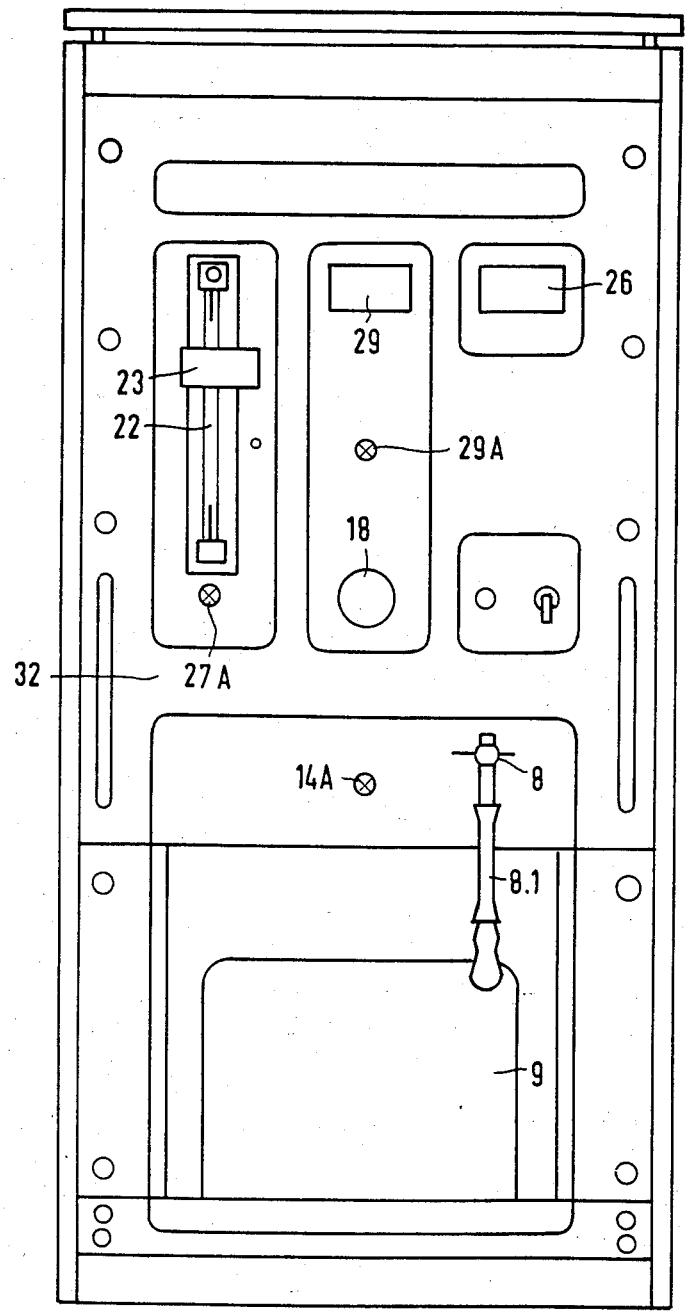
FIG. 2 is a top view from the front of a measuring cabinet for the sample-collecting system.

The system of the measuring gas cooler 5 is outlined by a dash-dotted frame. The gas line $g_2$ is conducted as a precipitation line through the heat-exchanging container 5a of the measuring gas cooler 5. The gas line $g_2$, runs downward in container 5a, at least in part as a helical tube coil 6.1, to a condensate collecting point 6, obtaining in the flow through the helical tube section 6.1 a cyclone separator effect for the $H_2O$ and $T_2O$ vapors and condensate contained in the measuring stream. A second rising branch 6.2 from the collecting point 6 is brought to the outside through the wall of the container 5a. The condensate of $H_2O$ and $T_2O$ resulting from cooling and separation in helical coil 6.1 falls to the collecting point 6 which is connected via the line section 6.3 to a fine-separating system 7, indicated only schematically, from which a condensate discharge line 7.1 with a drain valve 8 and a flexible line section 8.1 leads into a condensate collecting tank 9 which is located below the measuring gas cooler 5 and is shown filled with the condensate 10 of $H_2O$ and $T_2O$ more than half full to the level N. The collecting tank 9 rests on a spring-supported bottom 11 with the schematically indicated compression coil springs 12 supported on the floor surface 13. The level indicator, which is likewise fastened to the floor surface 13 engages the underside of the bottom 11 with a spring-loaded plunger 14.1 which is movable in the vertical direction. The plunger 14.1 actuates an end switch, not shown, of the filling level indicator 14 if the condensate in the collecting tank 9 has reached a certain level, at which level the liquid contents of tank 9 due to the force of gravity cause the tank 9 to move downward until the bottom 11 approaching the filling level indicator reaches the switching point of its end switch. Several switching points staggered relative to each other may be provided to warn not only that the collecting tank 9 is 95% filled, but also for instance, can indicate an 80% filling level as a preliminary warning. After the switch is actuated, the indication 14a "empty condensate" lights up on the front of the measuring cabinet (FIG. 2). The indicator lamp 14A is connected to the end switch of the filling level indicator 14 via the electric signal line e1.

Heat is transferred by cooling from the measurement gas flowing through the separator line 6.1 to a refrigerant fluid surrounding line 6.1 in the cooling space 5c of the container 5a. The refrigerant fluid is discharged through an external cooling branch 15, which is connected to the cooling chamber 5c by means of suitable connecting stubs with suction at 15b and pressure at 15a. The gaseous refrigerant in cooling chamber 5c such as Freon, flows from chamber 5c to the line section 15.1 and the connecting stub 15b to the suction side of the refrigeration compressor 16. The refrigerant is compressed and discharged through line 15.2 into condenser 17. Condenser 17 is exposed to a forced-air stream of a cooling-air blower, not shown. The heat of the refrigerant in the tube coils of the condenser 17, which is warmed due to the compression, is thereby carried to the outside. The arrows 17a symbolize the heat removal to the outside. The expansion of the refrigerant into the cooling chamber 5c of the container 5a takes place in the subsequent line section 15.3, and in particular through the opening 15a. The line section 15.3 is connected to a pressure gage 18 and the pressure recorded on gage 18 allows conclusions as to the proper operation of the cooling branch 15. The compressor 16 is shunted by a bypass 19 with a pressure control valve 20 to obtain a uniform refrigerant mass flow or a uniform cooling temperature. The valve 20 is controlled by the pressure on the suction ide of the compressor 16 and is actuated in the direction of closing if this pressure is too low and in the direction of opening if the suction pressure drops too much. Since the temperature has a proportional relationship with the refrigerant pressure, a constant temperature in the cooling chamber 5c of about 2° C. can be achieved thereby.

It is of great importance to keep constant and to regulate the measuring gas mass flow in the measuring gas line L2. The choke 21 in the measuring gas section L21 determines the flow resistance in the measuring gas line L2 in relation to the main stream line L1; this choke may be adjustable. In the example shown, 40% of the total flow $g_o$ goes through the measuring gas line L2, with the stream $g_1$ in the bypass line L 1 carrying about 60%. The flow transducer 22 which follows the choke 21 aids in controlling the gas mass flow. The desired amount, for instance 1 m$^3$ per hour, is fine-adjusted by the needle valve of the flow transducer (the choke 21 serves for the coarse adjustment). The flow transducer 22 is provided with a bistable ring initiator 23. Before discussing its operation, the pressure control by means of the bypass line L1 will be explained, by means of which the measuring gas pressure prevailing there is returned from the branching point 4 after the flow transducer 22 to a pressure difference control valve 24 on the pressure side of the measuring gas pump 2. The pressure on the output pressure side of the pump 2 is ascertained by means of the measuring line 24.1 and, if the pressure is too high, the control valve 24 is actuated in the opening direction and in the other case (pressure too low), in the closing direction.

By these three measures, namely, the choke 21, the flow transducer 22 with needle valve and the bypass pressure control L1, 24, 24.1, a high degree of constancy of the mass flow is achieved. The bypass pressure control is determined by the partial pressure and thus represents a temperature dependent control of the medium itself. The pressure of the pump 2 or 2' on the suction side is always provided because this pump operates under pressure, or in other words: the measuring gas is forced through the separating line $g_2$. This arrangement has substantial advantages with respect to the stability of operation and the operation overall as compared to suction operation because in suction operation, the partial pressure and the volume portions of the condensed vapors no longer exist after they flow through the measuring gas cooler.

Reverting to the ring initiator 23: The latter is connected via the signal line e2 to the semiconductor amplifier 25. If the metal sphere, not specifically shown, of the flow transducer 22 is located above the ring initiator 23 or below the same, a respective signal "max flow" and "min flow" is given which, after amplification, is present at the output of the amplifier 25 and serves as an alarm signal for the signal line e3 and also serves via the connecting line e4 for driving the operating hours counter 26. If the flow drops below the set value, the operating hour counter is shut off and the alarm indicator 27A activates flood lights. A similar situation applies if the flow rises above the set value. Further monitoring takes place via the temperature sensor 28 which ascertains the temperature in the cooling chamber 5c of the container 5, the measured value being fed via the signal line e5 to the temperature measuring device 29 with integrated limit indicator. The latter delivers at its output a warning signal to the line section e6 and thereby to the alarm or warning light 29A if an upper temperature limit, for instance, 3° C. or 2.5° C., is exceeded. As can be seen, a signal is present at the signal lights 27A, 29A and 14A if the measuring gas flow is too small or too large; the temperature of the coolant is too high; or the condensate filling level is too high. In addition, the corresponding signals are taken from the signal lines e3, e6 and e1 via the branch lines e71 to e73 and are fed to the inputs of a gate circuit 30 which gives a total indication via its output line e7 and the signal converter 31 to a control station (not shown). In particular, the gate circuit 30 is an OR gate. The three mentioned types of trouble sources, however, are also passed on separately by separate signal converters 27U, 29U and 14U from the lines e3, e6 and e1 and are passed-on to the line sections e31, e61 and e11 for remote transmission of the alarm signals. The measuring gas pumps 2 and 2', preferably, are multicell vacuum pumps. In such pumps, the working piston is supported, in particular, overhung on the motor shaft. This obviates an additional support in the side cover. The bearings of the drive motors are sealed against the working space of the vacuum pump. Contamination of the measurement gas by escaping bearing grease is therefore impossible.

FIG. 2 shows a measuring cabinet which has a front door 32 glazed with safety glass as well as a back door, both of which are provided with security locks. Also shown are the signal lights 27A, 29A and 14A and in the upper half the flow meter 22 with ring initiator 23, and next to it the pressure gage 18 and the temperature indicator 29; furthermore, in a panel next to it to the right, the operating-hour counter 26. In the lower half, the drain valve is followed by a flexible hose section 8.1 which is connected to a connecting stub of the condensate collecting tank 9.

The foregoing is a description corresponding, in substance, to German application P 33 21 063.2, dated June 10, 1983, internation priority of which is being claimed for the instant application and which is hereby made part of this application. Any material discrepancies between the foregoing specification and the specification of the aforementioned corresponding German application are to be resolved in favor of the latter.

There is claimed:

1. A sample collecting system for collecting gaseous or vaporous condensable radioactive substances in air from a nuclear installation which will operate over an extended monitoring period with no or few disturbances, and in the event that a disturbance occurs, gives at least one trouble signal, which comprises
- (a) a fine filter through which a gas stream of air containing gaseous or vaporous condensable radioactive substances passes for removal of entrained particles suspended in the gas stream
- (b) at least one suction branch line into which the filtered gas stream flows
- (c) a measuring gas pump in the suction branch line propelling the gas stream from the suction branch line through a precipitate line enclosed in a measuring gas cooler, said precipitate line extending downwardly in the measuring gas cooler, at least partially as a helical coil for condensing the condensable radioactive substances together with $H_2O$ if present and aiding in separating the condensate from the uncondensed gas in the gas stream
- (d) a condensate collecting point at about the lowest point of the precipitate line for discharge of the condensate from the precipitate line
- (e) a rising gas branch from the condensate collecting point upwards and then out of the measuring gas cooler for conducting the uncondensed gas from the condensate collecting point
- (f) a measuring gas choke in the measuring gas line for determining the flow resistance in that line, followed by a transducer which aids in controlling the gas mass flow, and following the transducer, the gas therefrom is returned to the source from which the gas stream for sampling was withdrawn
- (g) a pressure measuring line with a pressure difference control valve from the output of the flow transducer to the input of the precipitate line for regulating the measuring gas pressure of the measuring gas pump at the input of the precipitate line
- (h) at least one temperature sensor in the measuring gas cooler and temperature indicating means outside the measuring gas cooler for ascertaining the temperature and indicating if an upper temperature is exceeded
- (i) a fine separator system into which the condensate from the collecting point at the low point of the precipitate line flows
- (j) a condensate line with a drain valve through which the condensate from the fine separator system discharges
- (k) a condensate collecting tank located underneath the fine separtor system and into which the condensate from the condensate line flows, said tank also acting in determining the liquid level therein.

2. A sample collecting system according to claim 1, wherein the air to be sampled is exhaust air of a nuclear engineering installation and the radioactive substances contained in the exhaust air are molecules of $T_2O$ which are collected for determining traces of tritium in the exhaust air by means of the $T_2O$.

3. System according to claim 2, wherein the condensate-collecting vessel is supported on spring supports and the extent of movement of the vessel depending on the filling level or a part connected thereto is used for actuating an end switch which indicates the maximum filling level.

4. System according to claim 2, wherein the flow transducer is coupled to a bistable ring initiator which sends a signal via an amplifier to an operating-hours counter and if the gas flow falls below a set flow or exceeds a set flow the operating-hours counter is shut off and the amplifier delivers an alarm signal.

5. System according to claim 2, including a cabinet in a control room containing trouble signal means which show
    (a) if the gas flow as indicated by the flow transducer falls below a set flow or exceeds a set flow,
    (b) if the temperature indicated by the temperature sensor in the measuring gas cooler exceeds a set upper temperature, and
    (c) if the maximum filling level in the condensate-collecting vessel has been reached as indicated by movement of the vessel actuating a switch, and including a gate circuit for receiving signals originating in the flow transducer, temperature sensor and switch, and generating a collective indication of trouble signals which are passed on to the trouble signal means in the cabinet of the control room.

6. System according to claim 1, wherein the condensate-collecting vessel is supported on spring supports and the extent of movement of the vessel depending on the filling level or a part connected thereto is used for actuating an end switch which indicates the maximum filling level.

7. System according to claim 6, wherein the flow transducer is coupled to a bistable ring initiator which sends a signal via an amplifier to an operating-hours counter and if the gas flow falls below a set flow or exceeds a set flow the operating-hours counter is shut off and the amplifier delivers an alarm signal.

8. System according to claim 6, including a cabinet in a control room containing trouble signal means which show
    (a) if the gas flow as indicated by the flow transducer falls below a set flow or exceeds a set flow,
    (b) if the temperature indicated by the temperature sensor in the measuring gas cooler exceeds a set upper temperature, and
    (c) if the maximum filling level in the condensate-collecting vessel has been reached as indicated by movement of the vessel actuating a switch, and including a gate circuit for receiving signals originating in the flow transducer, temperature sensor and switch, and generating a collective indication of trouble signals which are passed on to the trouble signal means in the cabinet of the control room.

9. System according to claim 1, wherein the flow transducer is coupled to a bistable ring initiator which sends a signal via an amplifier to an operating-hours counter and if the gas flow falls below a set flow or exceeds a set flow the operating-hours counter is shut off and the amplifier delivers an alarm signal.

10. System according to claim 9, including a cabinet in a control room containing trouble signal means which show
    (a) if the gas flow as indicated by the flow transducer falls below a set flow or exceeds a set flow,
    (b) if the temperature indicated by the temperature sensor in the measuring gas cooler is a set upper tempearture, and
    (c) if the maximum filing level in the condensate-collecting vessel has been reached as indicated by movement of the vessel actuating a switch, and including a gate circuit for receiving signals originating in the flow transducer, temperature sensor and switch, and generating a collective indication of trouble signals which are passed on to the trouble signal means in the cabinet of the control room.

11. System according to claim 1, including a cabinet in a control room containing trouble signal means which show
   (a) if the gas flow as indicated by the flow transducer falls below a set flow or exceeds a set flow,
   (b) if the temperature indicated by the temperature sensor in the measuring gas cooler exceeds a set upper temperature, and
   (c) if the maximum filling level in the condensate-collecting vessel has been reached as indicated by movement of the vessel actuating a switch, and including a gate circuit for receiving signals originating in the flow transducer, temperature sensor and switch, and generating a collective indication of trouble signals which are passed on to the trouble signal means in the cabinet of the control room.

* * * * *